United States Patent
Zhang et al.

(10) Patent No.: US 11,240,865 B2
(45) Date of Patent: Feb. 1, 2022

(54) METHOD FOR DYNAMICALLY ADJUSTING A BLUETOOTH CONNECTION INTERVAL APPLIED TO ECG MEASURING INSTRUMENT

(71) Applicant: JIANGSU GAREA HEALTH TECHNOLOGY CO., LTD, Suzhou (CN)

(72) Inventors: Chunfeng Zhang, Suzhou (CN); Xiaodong Wang, Suzhou (CN); Jisong Hu, Suzhou (CN); Haofang Yang, Suzhou (CN)

(73) Assignee: JIANGSU GAREA HEALTH TECHNOLOGY CO., LTD, Suzhou (CN)

( * ) Notice: Subject to any disclaimer, the term of this patent is extended or adjusted under 35 U.S.C. 154(b) by 334 days.

(21) Appl. No.: 16/606,536

(22) PCT Filed: Jun. 10, 2019

(86) PCT No.: PCT/CN2019/090535
§ 371 (c)(1),
(2) Date: Oct. 18, 2019

(87) PCT Pub. No.: WO2020/052295
PCT Pub. Date: Mar. 19, 2020

(65) Prior Publication Data
US 2021/0136857 A1   May 6, 2021

(30) Foreign Application Priority Data
Sep. 12, 2018   (CN) .......................... 201811063470.7

(51) Int. Cl.
*H04W 76/20* (2018.01)
*H04W 76/19* (2018.01)
(Continued)

(52) U.S. Cl.
CPC ............. *H04W 76/20* (2018.02); *A61B 5/002* (2013.01); *A61B 5/0006* (2013.01); *H04W 4/80* (2018.02); *H04W 76/19* (2018.02); *H04W 84/18* (2013.01)

(58) Field of Classification Search
CPC ....... H04W 76/20; H04W 76/19; H04W 4/80; H04W 84/18; H04W 36/00; H04W 40/36;
(Continued)

(56) References Cited

U.S. PATENT DOCUMENTS

2009/0073870 A1* 3/2009 Haartsen ............... H04W 76/19
370/216
2011/0021142 A1   1/2011 Desai et al.
(Continued)

FOREIGN PATENT DOCUMENTS

CN   104601203 A   5/2015
CN   104639968 A   5/2015
(Continued)

OTHER PUBLICATIONS

Qin Haipeng, Design and Implementation of ECG Monitoring App Based On Android, Professional Master Dissertation , May 2017, Beijing University Of Technology, China.

*Primary Examiner* — Mewale A Ambaye
(74) *Attorney, Agent, or Firm* — Vivacqua Crane PLLC

(57) ABSTRACT

A method for dynamically adjusting a Bluetooth connection interval applied to an ECG measuring instrument includes: S1. initializing a Bluetooth module in a slave machine of the ECG measuring instrument, which enters an executable working status after self-inspection; S2. setting a Bluetooth system connection status based on a system status marking event sent from the slave machine to a master machine; S3. according to the connection status determined in step S2, the master machine and the slave machine entering a low-speed connection status after they complete data transmission in a (Continued)

high-speed connection status; S4. implementing interrupt processing between the master machine and the slave machine if no data transmission occurs between the master machine and the slave machine over 2 ms; and S5. going back to step S2 if the connection needs to be restored.

9 Claims, 2 Drawing Sheets

(51) Int. Cl.
  *H04W 4/80* (2018.01)
  *A61B 5/00* (2006.01)
  *H04W 84/18* (2009.01)
(58) Field of Classification Search
  CPC .... H04W 36/0033; A61B 5/0006; A61B 5/00; A61B 5/0245; A61B 5/28; A61B 2560/0209; A61B 5/002
  See application file for complete search history.

(56) References Cited

U.S. PATENT DOCUMENTS

| | | | | |
|---|---|---|---|---|
| 2011/0169654 | A1* | 7/2011 | Ketari | G08B 13/1427 340/687 |
| 2014/0329537 | A1* | 11/2014 | Huang | H04W 64/003 455/456.1 |

FOREIGN PATENT DOCUMENTS

| | | | |
|---|---|---|---|
| CN | 105451369 | A | 3/2016 |
| CN | 105575089 | A | 5/2016 |
| CN | 106073754 | * | 11/2016 |
| CN | 106073754 | A | 11/2016 |
| CN | 105451369 | * | 1/2018 |
| CN | 109104714 | A | 12/2018 |
| WO | 2014036955 | A1 | 3/2014 |

* cited by examiner

S1: Initializing a Bluetooth module in a slave machine of the ECG measuring instrument, the Bluetooth module entering an executable working status after self-inspection

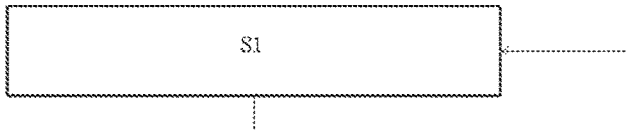

S21: Determining the type of the system status marking event

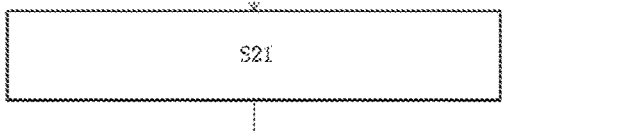

S22: Determining a transmission speed of data transmission of the event

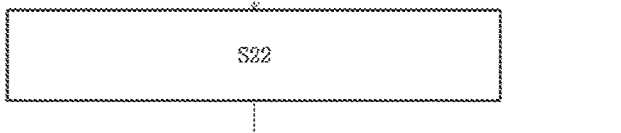

S23: Determining a transmission connection status type of the event

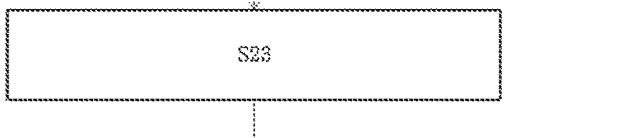

S24: For an event transmitted in a high-speed connection status, further adjusting a data connection interval of the event

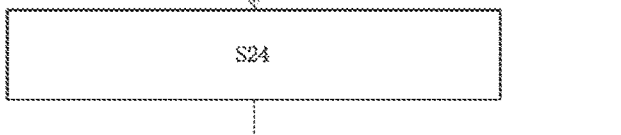

S3: according to the connection status determined in step S2, the master machine and the slave machine entering a low-speed connection status after they complete data transmission in a high-speed connection status

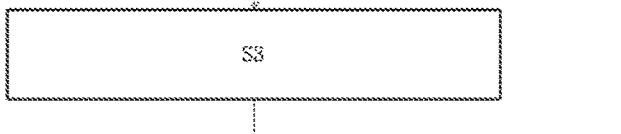

S4: after the master machine and the slave machine enter the low-speed connection status, implementing interrupt processing between the master machine and the slave machine if no data transmission occurs between the master machine and the slave machine over 2 ms

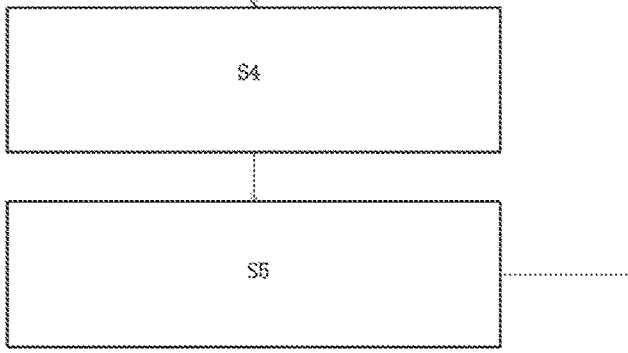

S5: after interrupt processing is implemented in step S4, going back to step S2 if the connection needs to be restored

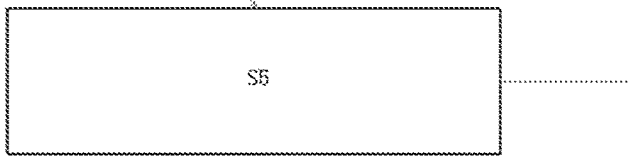

Fig.2

METHOD FOR DYNAMICALLY ADJUSTING A BLUETOOTH CONNECTION INTERVAL APPLIED TO ECG MEASURING INSTRUMENT

CROSS-REFERENCE TO RELATED APPLICATIONS

This application is a national stage application under 35 U.S.C. 371 of PCT Application PCT/CN2019/090535, filed on 10 Jun. 2019, which PCT application claimed the benefit of Chinese Patent Application No. 201811063470.7, filed on 12 Sep. 2018, the entire disclosure of each of which are hereby incorporated herein by reference.

FIELD

The disclosure relates to the field of wireless communication technologies, and in particular, to a method for dynamically adjusting a Bluetooth connection interval.

BACKGROUND

There are many kinds of Bluetooth low energy products on the market, which are applied in various fields. At present, low power consumption is a key technical issue of Bluetooth application products. For Bluetooth products, a button battery needs to satisfy the working requirement of maintaining a device for nearly a year, so power consumption is very critical for such products. The Bluetooth 4.0 version integrates the inherent advantages of the Bluetooth technology in wireless connection, and at the same time, incorporates the characteristics of high-speed Bluetooth and Bluetooth low energy. Bluetooth low energy is the core specification of Bluetooth 4.0. The biggest feature of this technology is its ultra-low operating power consumption and standby power consumption. Bluetooth low energy devices can work continuously for several years using a button battery, which can be applied to wireless solutions with strict requirements on cost and power consumption, and the development of smart phones will have a broader field.

A connection interval of a Bluetooth connection is a time interval between two connection events. The connection interval is based on 1.25 ms, and the connection interval has a value of 7.5 ms to 4 s, which must be an integer multiple of 1.25 ms. Different applications may require different time intervals. The advantage of a long time interval is significant power saving, since the device can have a long period of dormancy between connection events. The disadvantage is that when a device has application data to send, it has to wait for the next connection event, which reduces the efficiency of data transmission. The advantage of a short time interval is the frequent connection between two devices, which allows data to be sent and received more quickly. The disadvantage is that the devices are awakened frequently due to the arrival of connection events, which will consume more power.

The Bluetooth connection is applied to an ECG (electrocardiograph) measuring instrument, through which a slave machine of the ECG measuring instrument sends measurement data, historical data, and the like to a master machine. If the Bluetooth connection only uses a long time interval, it will lead to low data transmission efficiency, and even lead to data transmission congestion or data loss in case of urgent data transmission. If the Bluetooth connection only uses a short time interval, it will cause high energy consumption of the device and require frequent battery replacement, which will cause inconvenience to users. Therefore, how to balance energy consumption and the efficiency of data transmission of Bluetooth devices is an urgent technical problem to be solved.

SUMMARY

The technical problem to be solved in the disclosure is to propose a method for dynamically adjusting a Bluetooth connection interval applied to an ECG measuring instrument with respect to shortcomings of the prior art, for balancing energy consumption and the efficiency of data transmission of Bluetooth devices.

The disclosure adopts the following technical solution to solve the technical problem thereof.

There is provided a method for dynamically adjusting a Bluetooth connection interval applied to an ECG measuring instrument, including:

S1. initializing a Bluetooth module in a slave machine of the ECG measuring instrument, the Bluetooth module entering an executable working status after self-inspection;

S2. setting a Bluetooth system connection status based on a system status marking event sent from the slave machine to a master machine;

S3. according to the connection status determined in step S2, the master machine and the slave machine entering a low-speed connection status after they complete data transmission in a high-speed connection status;

S4. after the master machine and the slave machine enter the low-speed connection status, implementing interrupt processing between the master machine and the slave machine if no data transmission occurs between the master machine and the slave machine over 2 ms; and S5. after interrupt processing is implemented in step S4, going back to step S2 if the connection needs to be restored.

Further, the slave machine of the ECG measuring instrument communicates with the master machine of the ECG measuring instrument at a low data transmission rate.

Further, the system status marking event at least includes: real-time waveform transmission, historical data synchronization, a login page, and a historical data page.

Further, the system status marking event may further include sending the system status marking event; storing an ECG data event, storing ECG data; storing body temperature, heart rate, posture, abnormity type, and R-wave location data; ECG algorithms analysis; creating files; sending historical data; a low power consumption mode; interrupt processing setting an ECG data storage event; setting an ECG algorithm analysis event; setting a system status sending event; setting body temperature, heart rate, posture, abnormity type, and R-wave location data storage events; and setting file creation.

Further, step S2 further includes:

S21 determining the type of the system status marking event;

S22 determining a transmission speed of data transmission of the event;

S23 determining a transmission connection status type of the event; and

S24 for an event transmitted in a high-speed connection status, further adjusting a data connection interval of the event.

Further, the system status marking event in step S21 is divided into a data event and a control event; the data event involves real-time ECG signal transmission event; and the control event involves system control and conversion event.

Further, the transmission connection status type in step S23 includes a low-speed connection status and a high-speed connection status, and the data transmission speed in the low-speed connection status is lower than that in the high-speed connection status.

Further, a transmission connection status of a specific event is set to the low-speed connection status when the amount of data to be transmitted per second is less than a specific proportion of a Bluetooth transmission bandwidth.

Further, the specific proportion is any value between 60% and 45%; and the Bluetooth communication bandwidth is 4 KB.

There is further provided an ECG measuring instrument for executing the method for dynamically adjusting a Bluetooth connection interval, including an ECG signal acquisition circuit, an A/D conversion chip, a main control module, a Bluetooth communication module, and a master machine, wherein the main control module includes an ATBS module configured to execute step S2 in the method above.

The method for dynamically adjusting a Bluetooth connection interval applied to an ECG measuring instrument provided in the disclosure has the following beneficial effects. Through dynamic adjustment of Bluetooth connection, the requirements for measurement with ECG patches are met, the transmission bandwidth and the efficiency are increased by upshift, power consumption is reduced by downshift, and the service life is prolonged, so that the ECG patches can be more power-saving in use, thus avoiding frequent replacement.

BRIEF DESCRIPTION OF THE DRAWINGS

FIG. 2 is a flowchart of a method for dynamically adjusting a Bluetooth connection interval applied to an ECG measuring instrument according to the disclosure.

DETAILED DESCRIPTION OF THE EMBODIMENTS

Figure 1:
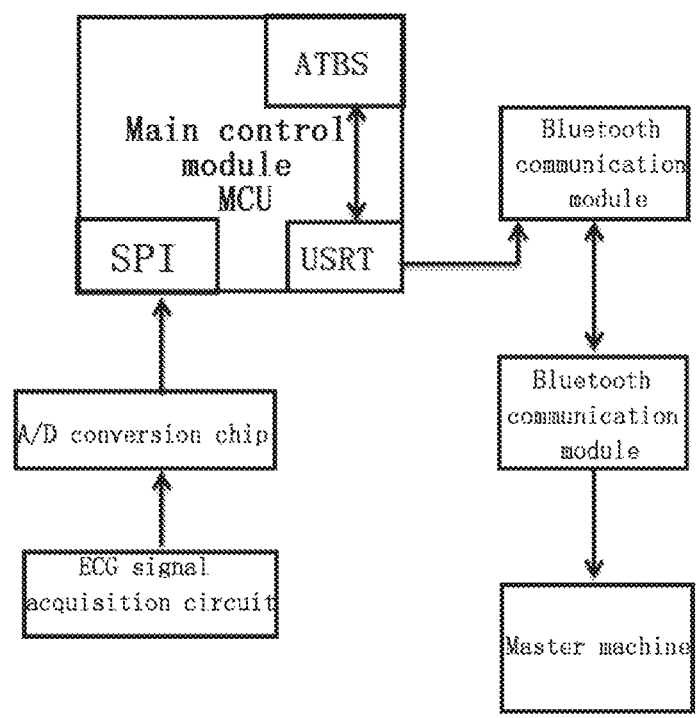
FIG. 1 is a schematic structural diagram of an ECG measuring instrument according to the disclosure.

The disclosure will be described in more detail below with reference to the accompanying drawings. Preferred embodiments of the disclosure are illustrated therein. It should be understood that those skilled in the art can amend the disclosure described here and still achieve the beneficial effects of the disclosure. Therefore, the following description shall be construed as a wide availability to those skilled in the art but not as a limitation to the disclosure.

For clarity, not all features of actual embodiments are described. In the following description, well-known functions and structures are not described in detail, as they would confuse the disclosure with unnecessary details. It should be considered that in the development of any actual embodiment, a lot of implementation details must be made to achieve the developer's specific objectives.

To make the objectives and features of the disclosure more comprehensible, embodiments of the disclosure are further explained below with reference to the accompanying drawings. It needs to be noted that the accompanying drawings are in a very simplified form and use an imprecise ratio, only for assisting in describing the objectives of embodiments of the disclosure conveniently and clearly.

In an embodiment, there is provided an ECG measuring instrument using a Bluetooth technology for communication, which, as shown in FIG. 1, has the following structure.

The ECG measuring instrument includes an ECG signal acquisition circuit, an A/D conversion chip, a main control module MCU, a Bluetooth communication module, and a master machine.

The ECG acquisition circuit is used to acquire ECG signals of a detected person. Preferably, the ECG acquisition circuit may also be provided with a filtering and common-mode ratio suppression module, so as to preliminarily process the initially measured ECG signals. Through the A/D conversion chip, analog signals acquired and processed by the ECG acquisition circuit are converted into digital signals and transmitted to a data register of the main control module MCU. ECG data acquired by the acquisition module is transmitted to the Bluetooth module through a UART interface of a main control chip. An SPI protocol built therein enables serial data transmission, and then the data is sent out by Bluetooth. The main control module MCU is provided with an ATBS module used to meet the requirements for measurement with ECG patches and dynamically adjust the bandwidth and interval of the Bluetooth connection. A specific adjustment manner for the ATBS module will be described in detail below.

Based on the above ECG measuring instrument, the disclosure further correspondingly provides a method for dynamically adjusting a Bluetooth connection interval applied to an ECG measuring instrument. As shown in FIG. 2, the method for dynamically adjusting a Bluetooth connection interval includes the following steps.

S1. A Bluetooth module in a slave machine of the ECG measuring instrument is initialized. The Bluetooth module may enter an executable working status after self-inspection, and the slave machine of the ECG measuring instrument communicates with the master machine of the ECG measuring instrument at a low data transmission rate.

S2. A connection status is determined based on a system status marking event sent from the slave machine to a master machine. The system status marking event may include real-time waveform transmission, historical data synchronization, a login page, and a historical data page. Preferably, the system status marking event may further include: 1) sending the system status marking event; 2) storing an ECG data event, storing ECG data; 3) storing body temperature, heart rate, posture, abnormity type, and R-wave location data; 4) ECG algorithm analysis; 5) creating files; 6) sending historical data; 7) a low power consumption mode; 8) interrupt processing; 9) setting an ECG data storage event; 10) setting an ECG algorithm analysis event; setting a system status sending event; setting body temperature, heart rate, posture, abnormity type, and R-wave location data storage events; 11) events such as setting file creation.

The method for determining a connection status based on a system status marking event may further include the following steps.

S21. The type of the system status marking event is determined, and the system status marking event is divided into a data event and a control event. The data event may specifically include events involving real-time ECG signal transmission such as real-time waveform transmission, historical data synchronization, and historical data transmission. The control event may specifically include system control and conversion events such as a login page, a historical data page, sending the system status marking event, storing ECG data events, storing ECG data, ECG algorithm analysis, and creating files.

The login page means that the master machine is on the login page.

The historical data page means that the master machine is on the historical data page.

The real-time waveform transmission status means displaying ECG data measured from the slave machine in real time on the master machine.

The historical data synchronization status means rapidly transmitting the ECG data measured from the slave machine to the master machine.

S22. A transmission speed of data transmission of the event is determined according to the type of the event determined in step S21.

The method provided in the disclosure proposes different algorithm of data transmission amount for different event types after making determination on the event type, thus optimizing the data transmission efficiency.

Specifically, for the data event, an ECG signal corresponding to one heartbeat is represented with H(n), and ECG signals in a period of time are represented with {H(n)} (n is 0, 1, 2 . . . ). According to a distribution pattern of the ECG signals, the amount of data sent by the ECG signals in 1 second, namely, the transmission speed, is:

$$H(N) = \sum_{n=0}^{N-1} H(n)\cos\left[\frac{(2n+1)\pi}{2N}\right]$$

where n denotes the number of each heartbeat, H(n) denotes the ECG signal corresponding to each heartbeat, and n denotes the total number of heartbeats included in the data within one second. N is between 50 to 90. For the control event, the number and size of packets contained in the event are detected, and the amount of data sent by the control event is obtained as:

$$P(N) = \sum_{n=0}^{N} P(n),$$

n is 0, 1, 2 . . . .

where n denotes the serial number of each packet, N denotes the total number of the packets, P(n) denotes the size of each packet, and P(N) denotes the sum of sizes of all packets.

Preferably, the transmission speed required by the control event can be calculated, through the control event, by dividing the sum of the amount of data transmitted by the control event by the required transmission time. The transmission time required by the control event can be obtained either by default or according to a conventional transport protocol.

S23 A transmission connection status type of the event is determined according to the data transmission speed calculated in step S22.

According to the data transmission amounts of the data event and the control event calculated in step S22, a transmission connection status type required is determined. The transmission connection status type may include a low-speed connection status and a high-speed connection status, and the data transmission speed in the low-speed connection status is lower than that in the high-speed connection status.

A transmission connection status of a specific event is set to the high-speed connection status when the amount of data to be transmitted per second is greater than or equal to a specific proportion of a Bluetooth transmission bandwidth.

The transmission connection status of the specific event is set to the low-speed connection status when the amount of data to be transmitted per second is less than the specific proportion of the Bluetooth transmission bandwidth. Specifically, the specific proportion can be any value between 60% and 45%. The Bluetooth transmission bandwidth is preferably 4 KB.

In addition, as an alternative embodiment, since the data transmission amount of ECG data is often large, in order to simplify the control calculation of the device, it is also possible to directly set the transmission connection status of the data event to the high-speed connection status.

S24. A data connection interval of an event transmitted in a high-speed connection status is further adjusted.

The transmission rate has the following relationship: (1 s/Bluetooth connection interval)*the number of packets sent per connection interval*the size of each packet. Therefore, the Bluetooth connection interval per second can be dynamically adjusted according to the data transmission speed per second obtained in step S22. In practical applications, sometimes data needs to be sent faster. At this time, the connection interval can be reduced to send data faster, but the power consumption is high. When the data is sent completely, the connection interval can be reduced to reduce power consumption and achieve equilibrium. For example, when a wearable device is connected, local data possibly needs to be sent to a mobile phone quickly, so that the connection interval can be set to be small. The interval is set to be large after the transmission is completed. In this way, the power consumption will not be too large. The connection interval refers to a periodic communication time after successful connection. The master machine may choose an appropriate interval time in this value range according to a usage situation. This specific value will affect the response time of the next communication packet. This range needs to be adjusted according to situations to achieve the purpose of saving energy and matching the response speed of the program.

Preferably, in this embodiment, 1.4 KB data per second needs to be transmitted in the real-time ECG waveform transmission status. In the historical data synchronization interface, in order to transmit the historical ECG data to the mobile phone quickly, the transmission rate is set to be 3.3 KB/s, and the maximum bandwidth of Bluetooth BLE is 4 KB/s. The maximum bandwidth can leave some margin, and due to the existence of the above margin, the connection interval may be set within a certain range, and the maximum and minimum values of the range are determined by calculation under the maximum bandwidth condition and under the maximum bandwidth condition with a certain margin, respectively. When the slave machine requests updating connection parameters, a minimum value and a maximum value are provided to the master machine. The master machine will negotiate according to the two values provided by the slave machine, and eventually choose an appropriate value within this range as the final connection interval. In this system, the minimum connection interval is set to be 10 ms, and the maximum connection interval is set to be 20 ms. Finally, the master machine may work in a transmission status with a connection interval of 15 ms and sends 3 packets per second, each packet being 20 B, and thus the transmission rate is: (1/15)*3*20=4 KB/s.

The above step S2 is preferably executed by the ATBS module in the main control module MCU.

S3. According to the connection status determined in step S2, the master machine and the slave machine enter a low-speed connection status after they complete data transmission in a high-speed connection status.

Specifically, the historical data synchronization status is switched to the real-time waveform transmission status from 3.3 K/s to 1.4 K/s, the real-time waveform transmission status is switched to the login page, the historical data page is adjusted to the low-speed status from 1.4 K/s, the login page and the historical data page are switched to the real-time waveform transmission status from the low speed to 1.4 K/s, the historical data synchronization status is switched to the login page, the historical data page is adjusted to the low speed from 3.3 K/s, and the login page and the historical data page are switched to the historical data synchronization status to 3.3 K/s from the low speed.

S4. After the master machine and the slave machine enter the low-speed connection status, interrupt processing is implemented between the master machine and the slave machine if no data transmission occurs between the master machine and the slave machine over 2 ms.

S5. After interrupt processing is implemented in step S4, go back to step S2 if the connection needs to be restored.

The method for dynamically adjusting a Bluetooth connection interval applied to an ECG measuring instrument provided in the disclosure has the following beneficial effects. Through dynamic adjustment of Bluetooth connection, the requirements for measurement with ECG patches are met, the transmission bandwidth and the efficiency are increased by upshift, power consumption is reduced by downshift, and the service life is prolonged, so that the ECG patches can be more power-saving in use, thus avoiding frequent replacement.

Those skilled in the art should understand that the embodiments of this application can be provided as a method, an apparatus, or a computer program product. Therefore, this application may be implemented in a form of a complete hardware embodiment, a complete software embodiment, or an embodiment combining software and hardware. Moreover, this application can be in the form of a computer program product implemented on one or more computer usable storage media (including, but not limited to, a magnetic disk memory, a CD-ROM, an optical memory and the like) including computer usable program codes.

The above shows and describes the basic principle, main features and advantages of the disclosure. Those skilled in the art should understand that the disclosure is not limited by the above embodiments. Only the principle of the disclosure is described in the above embodiments and the specification. The disclosure may further have various changes and improvements without departing from the principle and scope of the disclosure. The protection scope of the present invention is defined by the appended claims and equivalents thereof.

The invention claimed is:

1. A method for dynamically adjusting a Bluetooth connection interval applied to an electrocardiograph (ECG) measuring instrument, comprising:
S1. initializing a Bluetooth module in a slave machine of the ECG measuring instrument, the Bluetooth module entering an executable working status after self-inspection;
S2. setting a Bluetooth system connection status based on a system status marking event sent from the slave machine to a master machine;
S3. according to the connection status determined in step S2, the master machine and the slave machine entering a low-speed connection status after they complete data transmission in a high-speed connection status;
S4. after the master machine and the slave machine enter the low-speed connection status, implementing interrupt processing between the master machine and the slave machine if no data transmission occurs between the master machine and the slave machine over 2 millisecond (ms); and
S5. after interrupt processing is implemented in step S4, going back to step S2 if the connection needs to be restored;
wherein step S2 further comprises:
S21. determining a type of the system status marking event;
S22. determining a transmission speed of data transmission of the event;
S23. determining a transmission connection status type of the event; and
S24. for an event transmitted in a high-speed connection status, further adjusting a data connection interval of the event.

2. The method according to claim 1, wherein the slave machine of the ECG measuring instrument communicates with the master machine of the ECG measuring instrument at a low data transmission rate.

3. The method according to claim 1, wherein the system status marking event at least comprises: real-time waveform transmission, historical data synchronization, a login page, and a historical data page.

4. The method according to claim 1, wherein the system status marking event further comprises: sending the system status marking event; storing an ECG data event, storing ECG data; storing body temperature, heart rate, posture, abnormity type, and R-wave location data; ECG algorithm analysis; creating files; sending historical data; a low power consumption mode; interrupt processing; setting an ECG data storage event; setting an ECG algorithm analysis event; setting a system status sending event; setting body temperature, heart rate, posture, abnormity type, and R-wave location data storage events; and setting file creation.

5. The method according to claim 1, wherein the system status marking event in step S21 is divided into a data event and a control event; the data event involves real-time ECG signal transmission event; and the control event involves system control and conversion event.

6. The method according to claim 1, wherein the transmission connection status type in step S23 comprises a low-speed connection status and a high-speed connection status, and data transmission speed in the low-speed connection status is lower than that in the high-speed connection status.

7. The method according to claim 6, wherein a transmission connection status of a specific event is set to be the low-speed connection status when the amount of data to be transmitted per second is less than a specific proportion of a Bluetooth transmission bandwidth.

8. The method according to claim 7, wherein the specific proportion is any value between 60% and 45%; and the Bluetooth communication bandwidth is 4 KB.

9. An ECG measuring instrument for executing method for dynamically adjusting a Bluetooth connection interval, comprising, an ECG signal acquisition circuit, an analog to digital (A/D) conversion chip, a main control module, a Bluetooth communication module, and a master machine, wherein the main control module comprises an automatic tune bandwidth system (ATBS) module, wherein the ECG measuring instrument comprising:

S1. initializing a Bluetooth module in a slave machine of the ECG measuring instrument, the Bluetooth module entering an executable working status after self-inspection;

S2. setting a Bluetooth system connection status based on a system status marking event sent from the slave machine to a master machine;

S3. according to the connection status determined in step S2, the master machine and the slave machine entering a low-speed connection status after they complete data transmission in a high-speed connection status;

S4. after the master machine and the slave machine enter the low-speed connection status, implementing interrupt processing between the master machine and the slave machine if no data transmission occurs between the master machine and the slave machine over 2 millisecond (ms); and S5. after interrupt processing is implemented in step S4, going back to step S2 if the connection needs to be restored;

wherein step S2 further comprises:

S21. determining a type of the system status marking event;

S22. determining a transmission speed of data transmission of the event;

S23. determining a transmission connection status type of the event; and

S24. for an event transmitted in a high-speed connection status, further adjusting a data connection interval of the event.

* * * * *